(12) United States Patent
Lee et al.

(10) Patent No.: US 10,492,285 B2
(45) Date of Patent: Nov. 26, 2019

(54) PLASMA ELECTRODE DEVICE, METHOD OF MANUFACTURING PLASMA ELECTRODE DEVICE, AND AIR CONDITIONER

(71) Applicant: LG ELECTRONICS INC., Seoul (KR)

(72) Inventors: Sanggu Lee, Seoul (KR); Jaesoo Jang, Seoul (KR); Bongjo Sung, Seoul (KR); Chulwoo Park, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 288 days.

(21) Appl. No.: 15/369,381

(22) Filed: Dec. 5, 2016

(65) Prior Publication Data

US 2017/0165606 A1    Jun. 15, 2017

(30) Foreign Application Priority Data

Dec. 9, 2015  (KR) .......................... 10-2015-0175183

(51) Int. Cl.
*B01D 53/32*    (2006.01)
*H05H 1/24*    (2006.01)
(Continued)

(52) U.S. Cl.
CPC ............. *H05H 1/2406* (2013.01); *A61L 9/03* (2013.01); *A61L 9/22* (2013.01); *B01D 53/32* (2013.01);
(Continued)

(58) Field of Classification Search
CPC .......... H05H 1/2406; A61L 9/22; A61L 9/03; B01D 53/32; F24F 3/166
See application file for complete search history.

(56) References Cited

U.S. PATENT DOCUMENTS 7,294,176 B2    11/2007  Kim et al.
8,400,751 B2 *   3/2013  Tanaka ................... H05K 13/00
                                            361/230
(Continued)

FOREIGN PATENT DOCUMENTS

JP    2015-188882    11/2015
JP    2015-195162    11/2015
(Continued)

OTHER PUBLICATIONS

Korean Office Action dated Mar. 17, 2017 issued in Application No. 10-2015-0175183.
(Continued)

*Primary Examiner* — Regina M Yoo
(74) *Attorney, Agent, or Firm* — Ked & Associates LLP (57) ABSTRACT

A plasma electrode device, a method of manufacturing plasma electrode device, and an air conditioner are provided. The plasma discharge device may include an insulating body; a discharge electrode formed in a first surface of the insulating body to generate plasma discharge; and a ground electrode formed in a second surface of the insulating body to generate plasma discharge by reacting with the discharge electrode. The discharge electrode may have a prescribed pattern having a plurality of branches, and the insulating body may include a flexible material configured to be curved at a predetermined curvature.

7 Claims, 6 Drawing Sheets

(51) Int. Cl.
*A61L 9/03* (2006.01)
*F24F 3/16* (2006.01)
*A61L 9/22* (2006.01)

(52) U.S. Cl.
CPC .......... *F24F 3/166* (2013.01); *A61L 2209/16* (2013.01); *A61L 2209/212* (2013.01); *B01D 2259/818* (2013.01); *F24F 2003/1671* (2013.01); *F24F 2003/1682* (2013.01); *F24F 2003/1685* (2013.01); *H05H 2001/2412* (2013.01); *H05H 2245/121* (2013.01)

(56) References Cited

U.S. PATENT DOCUMENTS

| | | | | |
|---|---|---|---|---|
| 9,457,118 | B2* | 10/2016 | Ota | B03C 3/09 |
| 9,694,369 | B2* | 7/2017 | Engberg | B03C 3/011 |
| 2005/0231884 | A1* | 10/2005 | Miyaishi | A61L 9/22 |
| | | | | 361/231 |
| 2006/0056129 | A1 | 3/2006 | Kim et al. | |
| 2011/0102963 | A1* | 5/2011 | Sekoguchi | A61L 9/22 |
| | | | | 361/230 |
| 2011/0115362 | A1* | 5/2011 | Sekoguchi | B03C 3/383 |
| | | | | 313/230 |
| 2015/0137677 | A1* | 5/2015 | Sohn | H01T 19/04 |
| | | | | 313/268 |
| 2015/0279622 | A1* | 10/2015 | Jang | A61L 2/088 |
| | | | | 313/231.61 |
| 2016/0015843 | A1* | 1/2016 | Jang | B03C 3/12 |
| | | | | 62/264 |
| 2016/0015848 | A1* | 1/2016 | Jung | H05H 1/2406 |
| | | | | 422/121 |
| 2017/0341087 | A1* | 11/2017 | Yuge | B03C 3/025 |
| 2017/0346261 | A1* | 11/2017 | Haruna | A61L 9/22 |

FOREIGN PATENT DOCUMENTS

| | | | | |
|---|---|---|---|---|
| KR | 10-2006-0024845 | | 3/2006 | |
| KR | 10-0657476 | | 12/2006 | |
| KR | 10-0861559 | | 10/2008 | |
| KR | 10-2015-0053136 | | 5/2015 | |
| WO | WO-2013161534 A1 | * | 10/2013 | .............. B03C 3/09 |
| WO | WO-2013191499 A1 | * | 12/2013 | ............ F24F 1/0011 |

OTHER PUBLICATIONS

PCT International Search Report dated Apr. 7, 2017 issued in Application No. PCT/KR2016/014150.

* cited by examiner

PLASMA ELECTRODE DEVICE, METHOD OF MANUFACTURING PLASMA ELECTRODE DEVICE, AND AIR CONDITIONER

CROSS-REFERENCE TO RELATED APPLICATION(S)

The present application claims priority under 35 U.S.C. 119 and 35 U.S.C. 365 to Korean Patent Application No. 10-2015-0175183 filed in Korea on Dec. 9, 2015, which is hereby incorporated by reference in its entirety.

BACKGROUND

1. Field

A plasma electrode device, a method of manufacturing a plasma electrode device, and an air conditioner are disclosed herein.

2. Background

Recently, buildings have been constructed to minimize introduction of external air and to tightly seal an indoor space in order to reduce energy consumption, and therefore, there is a tendency for pollution of indoor air to increase. Therefore, various legal regulations with respect to indoor contaminants are increasingly being reinforced.

While home appliances installed in homes or companies operate, indoor contaminants may be generated and deposited within the home appliances or discharged from the home appliances. The indoor contaminants may cause an unpleasant odor and have a bad impact on a user's health.

For example, in a case of home electric appliances using air containing moisture or water, such as air conditioners, dehumidifiers, air cleaners, refrigerators, or washing machines, for example, pollution may be caused by dust or microorganisms, for example, inside or outside of the home electric appliances. More specifically, the indoor contaminants may be classified into (1) particulate contaminants, such as fine dust or asbestos, for example, (2) gaseous contaminants, such as Carbon dioxide, formaldehyde, or volatile organic compounds (VOC), for example, and (3) biological contaminants, such as viruses, fungi, or bacteria, for example.

A creeping discharge type plasma chemical processing method may be used in order to remove such indoor contaminants. Generally, the creeping discharge type plasma chemical processing method may refer to a method of forming a high density plasma region on an element surface through high frequency discharge using ceramic to generate a large amount of OH radicals and ozone and removing contaminants using the OH radical and ozone.

On the other hand, the ozone generated in the plasma electrode device has a sterilization effect. Therefore, when a small amount of ozone exists in air, a user may feel refreshed. However, when a predetermined amount or more of ozone exists in air, the user may feel uncomfortable, and when the user breathes the ozone for a long period of time, respiratory organs of the user may be damaged. Therefore, it is necessary to appropriately adjust the amount of ozone generated by the plasma electrode device.

In connection with the above technology, the present applicant has filed an application (hereinafter, referred to as "related art"), registered as Korean Patent Registration No. 10-0657476 on Dec. 7, 2006 and entitled "CREEPING DISCHARGE TYPE AIR CONDITIONER", which is hereby incorporated by reference. The above-described related art discloses a plasma electrode device including a discharge electrode disposed on a top surface of two sheets of insulating dielectrics, which are attached to each other, a ground electrode disposed between the two sheets of insulating dielectrics, and a coating layer that shields the discharge electrode to prevent the discharge electrode from being directly exposed to air. The insulating dielectrics may be coated by an insulating material. For example, the insulating material may include polyvinyl chloride (PVC) or ceramic, for example.

When a high voltage is applied to the plasma electrode device, there are problems that a noise may occur upon operation of the plasma electrode device and plasma discharge stability may decrease. Further, the insulating dielectric used in the plasma electrode device according to the related art is formed of a resin having a low flexibility, such as PVC or ceramic. Therefore, there is a problem that it is difficult to mount the plasma electrode device on a curved surface when mounting it on an air conditioner, for example.

BRIEF DESCRIPTION OF THE DRAWINGS

Embodiments will be described in detail with reference to the following drawings in which like reference numerals refer to like elements, and wherein.

DETAILED DESCRIPTION

Hereinafter, embodiments will be described with reference to accompanying drawings. It will be understood that the description herein is not intended to limit the claims to the embodiments described. On the contrary, it is intended to cover alternatives, modifications, and equivalents as may be included within the spirit and scope of the present disclosure as defined by the appended claims.

Figure 1:
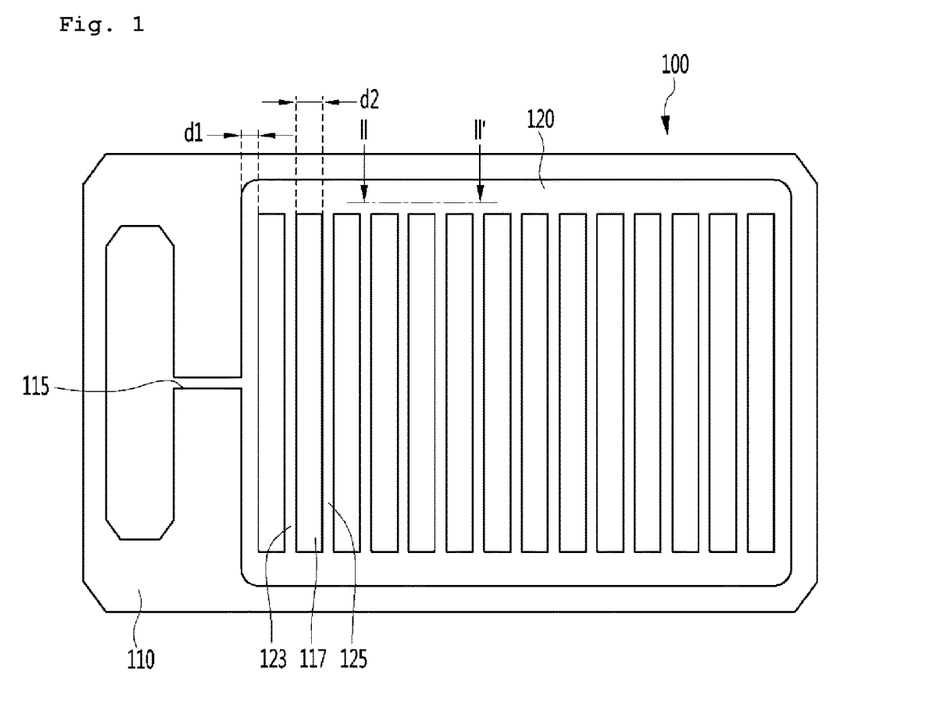
FIG. 1 is a view of a plasma electrode device according to an embodiment.
Figure 2:
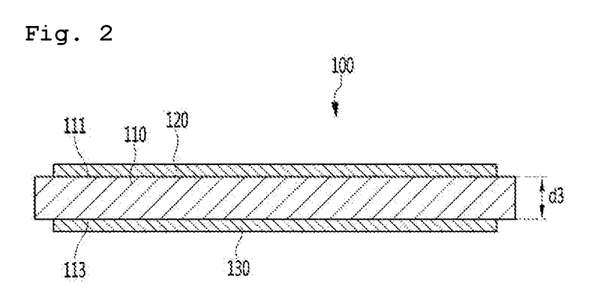
FIG. 2 is a cross-sectional view, taken along line II-II' of FIG. 1.

FIG. 1 is a view of a plasma electrode device according to an embodiment. FIG. 2 is a cross-sectional view, taken along line II-II' of FIG. 1.

Referring to FIGS. 1 and 2, the plasma electrode device 100 according to an embodiment may include an insulating body 110, a discharge electrode 120, and a ground electrode 130. The insulating body 110 may have a rectangular plate shape, as illustrated in FIG. 1, and may have an upper surface 111 and a lower surface 113. The shape of the insulating body 110 is not limited thereto, and may have an appropriate shape depending on design conditions. The upper surface 111 and the lower surface 113 of the insulating body 110 may be referred to as one or a first surface 111 and the other or a second surface 113 of the insulating body 110.

The discharge electrode 120 and the ground electrode 130 may be provided in the upper surface 111 or the lower surface 113 of the insulating body 110. More specifically, the discharge electrode 120 and the ground electrode 130 may be coated on the insulating body 110 by micro electro mechanical systems (MEMS), for example.

The micro electro mechanical systems, namely, MEMS uses the micro process technology in semiconductor device fabrication, in which deposition and etching processes are repeatedly performed. A micro-mechanical structure manufactured by the MEMS has precision of micrometers or less. The MEMS processing makes mass production of super-fine mechanical structures possible at low cost.

The insulating body 110 may be provided with an electrode portion 115 connected to a power supply, and the discharge electrode 120 may be connected to the electrode portion 115 and may be supplied with power. The discharge electrode 120 may extend from the electrode portion 115. The discharge electrode 120 may generate plasma discharge to oxidize or decompose air flowing around the discharge electrode 120 when a voltage is applied thereto through the electrode portion 115.

The discharge electrode 120 may include a pattern having a plurality of branches on the upper surface 111 of the insulating body 110. More specifically, the discharge electrode 120 may be formed by being patterned on a surface of the insulating body 110 with a conductive material, such as a metal material. For example, the discharge electrode 120 may be a metal plate, for example, Cu.

The pattern of the discharge electrode 120 may have a closed shape having a prescribed or predetermined area. For example, the pattern of the discharge electrode 120 may have a trapezoid shape.

A width d1 of the pattern of the discharge electrode 120 may be equal to or less than 100 micrometers. That is, the width d1 of the pattern of the discharge electrode 120 may be dozens of micrometers. This is possible by manufacturing the discharge electrode 120 by the MEMS.

As the width d1 of the pattern of the discharge electrode 120 decreases, the discharge electrode 120 has a larger discharge area, enabling generation of high-density radicals and ensuring a large discharge area, compared to the area of the insulating body 110.

The pattern of the discharge electrode 120 may include a non-patterned portion 117, in which no electrode is formed therein. More specifically, the non-patterned portion 117 may be provided between a plurality of branches 123 and 125 forming the pattern of the discharge electrode 120.

A plurality of non-patterned portions 117 may be provided and may be formed such that widths d2 of the plurality of non-patterned portions 117 are equal to one another. That is, distances (widths d2) between the plurality of branches 123 and 125 forming the pattern of the discharge electrode 120 may be formed equally, thus enhancing plasma discharge stability.

The ground electrode 130 may be provided on the lower surface 113 of the insulating body 110. The ground electrode 130 may generate plasma discharge by acting with the discharge electrode 120, The ground electrode 130 may have a prescribed or predetermined pattern, like the discharge electrode 120. The pattern of the ground electrode 130 may be smaller than the pattern of the discharge electrode 120.

As a gap between the discharge electrode 120 and the ground electrode 130 becomes narrower, a voltage applied for the plasma discharge may be decreased. When a thickness d3 of the insulating body 110 becomes thinner, it is possible to reduce a voltage applied to the plasma electrode device 100.

More specifically, the thickness d3 of the insulating body 110 may be equal to or less than 100 micrometers. That is, the insulating body 110 may have a thickness d3 of dozens of micrometers. This is possible only when the insulating body 110 is formed of a material with sufficient thermal resistance, chemical resistance, and impact resistance to bear the MEMS processing.

A method of coating the discharge electrode 120 on the insulating body 110 by the MEMS will be described hereinafter.

Figure 3:
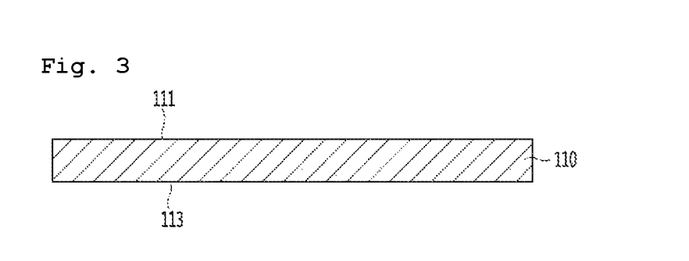
FIGS. 3 to 5 are diagrams illustrating a process of forming a discharge electrode on an insulating body by microelectro mechanical systems (MEMS)
Figure 4:
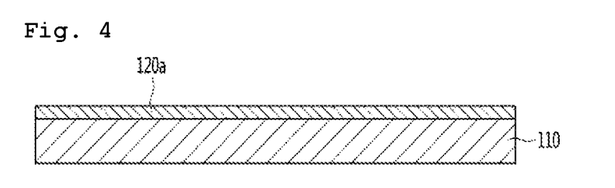
Figure 5:
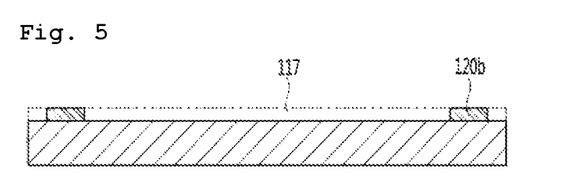

FIGS. 3 to 5 are diagrams illustrating a process of forming a discharge electrode on an insulating body by MEMS. More specifically, FIG. 3 illustrates an insulating body. FIG. 4 is a diagram for describing a process of depositing a metal plate on one or a first side of the insulating body. FIG. 5 is a diagram for describing a process of forming a discharge electrode with a pattern by etching a partial portion of a metal plate.

Referring to FIGS. 3 to 5, when an insulating body, such as insulating body 110 of FIGS. 1-7, having a prescribed or predetermined thickness is provided, a metal plate 120a may be deposited on an upper surface 111 of the insulating body 110 and etching may be performed to form a portion at which the discharge electrode 120 does not exist on the upper surface 111 of the insulating body 110, such as non-patterned portion 117 of FIG. 1. Etching schemes may include dry etching using plasma and wet etching using chemical solutions, for example. Thus, a pattern portion 120b of the discharge electrode 120, which has a fine size, may be formed in or on the upper surface 111 of the insulating body 110.

In order to prevent damage during deposition and etching upon MEMS processing, the insulating body 110 may be formed of or include a material with thermal resistance and chemical resistance. For example, the insulating body 110 may be formed of or include polyimide resin. The polyimide resin exhibits 1) excellent thermal resistance, 2) a small change in characteristics as temperature varies from a low temperature to a high temperature, 3) excellent impact resistance and high dimensional stability, 4) excellent electrical characteristics, 5) excellent chemical resistance, and 6) excellent abrasion resistance and nonflammability.

On the other hand, when the insulating body 110 is formed of a material with low thermal resistance and low chemical resistance, there may occur a problem that the insulating body 110 is damaged during deposition and etching when the discharge electrode 120 and the ground electrode 130 are coated on a surface of the insulating body 110 in the MEMS processing. When the insulating body 110 is formed of polyimide resin with high thermal resistance and high chemical resistance, damage due to the MEMS processing may be minimized.

Also, as the polyimide resin has excellent impact resistance and excellent abrasion resistance, it is possible to manufacture a thin film using the polyimide resin. Thus, when the insulating body 110 is formed of the polyimide resin, the insulating body 110 may be manufactured to have a thin thickness. Therefore, it is possible to reduce an input voltage by reducing a gap between the discharge electrode 120 and the ground electrode 130. In a case of manufacturing the insulating body 110 using the polyimide resin, it is possible to allow the insulating body 110 to have a thickness of dozens of micrometers.

In addition, as the polyimide resin is flexible, the insulating body 110 may be bendable at or to a prescribed or predetermined curvature when the insulating body 110 is formed of the polyimide resin. Therefore, it is possible to mount the plasma electrode device 100 on a curved mounting surface. Mounting of the plasma electrode device 100 will be described hereinafter with reference to FIG. 6.

The ground electrode 130 may be formed on the lower surface 113 of the insulating body 110 by the MEMS, like the discharge electrode 120, and therefore, a detailed description thereof has been omitted.

An air conditioner in which the plasma electrode device 100 is mounted will be described hereinafter.

Figure 6:
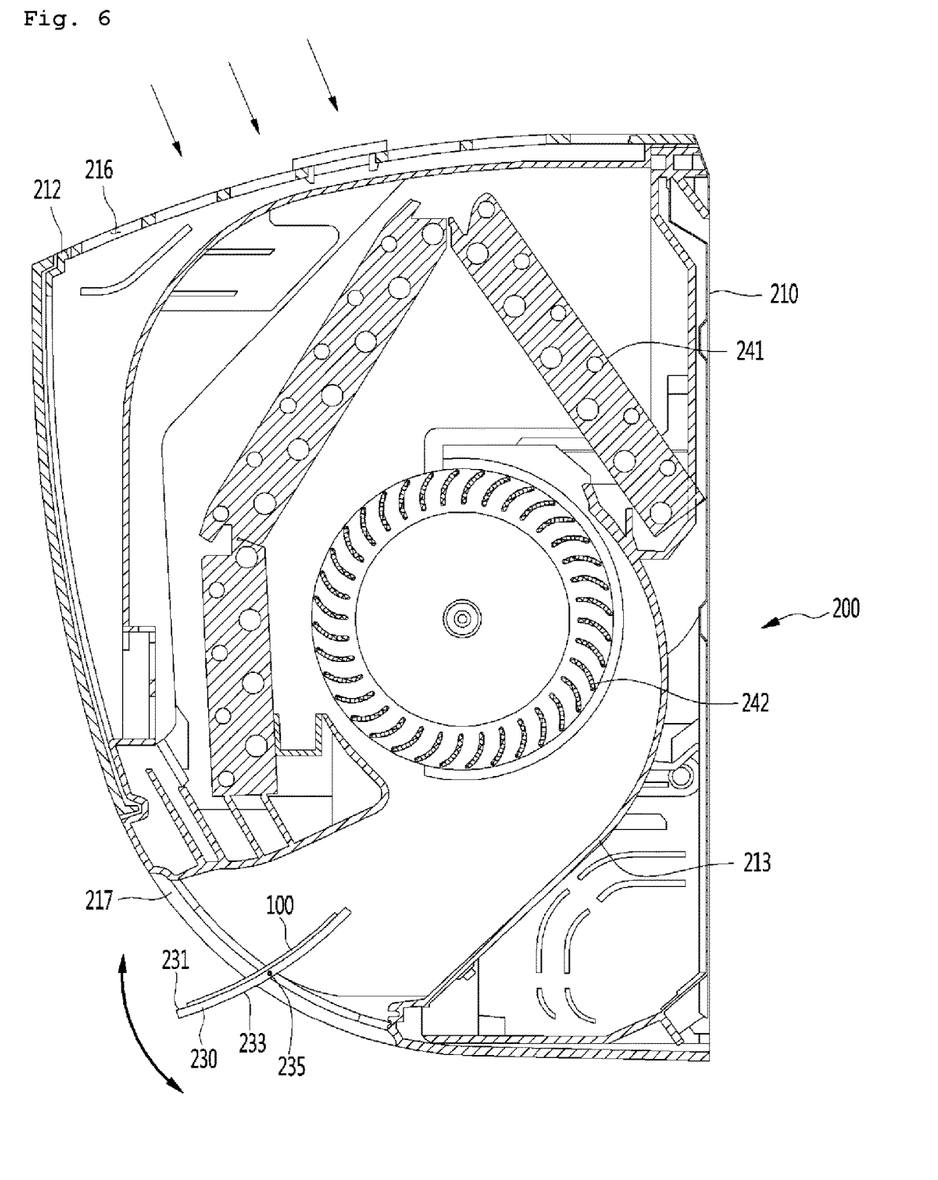
FIG. 6 is a diagram illustrating a plasma electrode device mounted on an air conditioner according to an embodiment.

FIG. 6 is a diagram for describing a plasma electrode device mounted on an air conditioner according to an embodiment. Referring to FIG. 6, the air conditioner 200 according to an embodiment may include a main body 210 in which a plurality of components may be received including plasma electrode device 100. The plasma electrode device 100 may be mounted on the main body 210 to remove contaminants or odors through ion generation.

The main body 210 may include a front frame 212 and a rear frame 213 defining an outer appearance of the main body 210. A space in which various types of components may be mounted may be provided between the front frame 212 and the rear frame 213. In the inner space of the main body 210, there may be provided an indoor heat exchanger 241 in which heat exchange may be made between indoor air and a refrigerant and a fan 242 configured to cause indoor air to flow forcibly. The main body 210 may include an air inlet 216, through which indoor air may be suctioned into the inner space, and an air outlet 217, through which the suctioned indoor air having been conditioned may be discharged.

The air conditioner 200 may further include a discharge vane 230 provided in or at one side of the air outlet 217. The discharge vane 230 may have an inner surface 231 facing an inside of the main body 210 and an outer surface 233 facing an outside of the main body 210. The inner surface 231 and the outer surface 233 of the discharge vane 230 may have a curved surface with a prescribed or predetermined curvature.

The discharge vane 230 may be connected to the main body 210 through a hinge shaft 235 and may be rotated around the hinge shaft 235. The discharge vane 230 may guide a discharge direction of air caused to flow by the fan 242.

The plasma electrode device 100 may be mounted on the discharge vane 230. Therefore, contaminants and odors included in air discharged from the air outlet 217 may be removed, and ions generated from or by the plasma electrode device 100 may be supplied to the indoor space due to air flow generated by the fan 242.

The plasma electrode device 100 may be mounted on the inner surface 231 of the discharge vane 230. Therefore, the plasma electrode device 100 may not be exposed to the outside, and at the same time, the ions generated by the plasma electrode device 100 may be effectively scattered.

By forming the plasma electrode device 100 of a flexible material, the plasma electrode device 100 may be curved corresponding to a shape of the inner surface 231 of the discharge vane 230. It is noted that a mounting position of the plasma electrode device 100 is not limited to the inner surface 231 of the discharge vane 230 and may be changed depending on design. That is, the plasma electrode device 100 may be mounted on or in a path of air flow generated by the fan 242.

As another embodiment, the plasma electrode device 100 may be disposed or provided between the air inlet 216 and the indoor heat exchanger 241 unlike what is illustrated. More specifically, the plasma electrode device 100 may be disposed or provided inside of the indoor heat exchanger 241 or the front frame 212. When the plasma electrode device 100 is disposed or provided adjacent to the air inlet 216, internal sterilization of the air conditioner 200 may be possible and removal of floaters may be facilitated. As another embodiment, the plasma electrode device 100 may be disposed or provided between the fan 242 and the air outlet 217.

As described above, the plasma electrode device according to embodiments may be formed of or include a flexible material, and therefore, the plasma electrode device according to embodiments may be mounted on a curved surface as well as a flat surface, thus enhancing mounting freedom. Also, it is possible to remove a necessity to form the plasma electrode device to have a curved surface, thus reducing manufacturing cost.

According to embodiments, it is possible to generate plasma discharge using a lower voltage, compared to the related art, improve stability, and reduce a noise and ozone occurring upon discharge. Also, the plasma electrode device according to embodiments may be mounted on a curved surface as the plasma electrode device may be formed of a flexible material, thus ensuring mounting freedom.

By coating the discharge electrode on the insulating body through the MEMS processing, the discharge electrode may be formed to have a narrow width, thus increasing a discharge region. Also, by providing discharge electrodes at uniform intervals, it is possible to ensure plasma discharge stability.

Embodiments disclosed herein improve mounting freedom of a plasma electrode device upon mounting on or in an air conditioner, for example, by forming the plasma electrode device using a flexible material. Further, embodiments disclosed herein provide a plasma electrode device in which discharge is generated even by a relatively low voltage. Furthermore, embodiments disclosed herein a large discharge region compared to an area of a mounting region of a discharge electrode. Embodiments disclosed herein also ensure plasma discharge stability.

However, embodiments disclosed herein are not limited to the above-described purposes, and other purposes not described will be clearly understood by those of ordinary skill in the art from the description.

In order to improve mounting freedom of a plasma electrode device, a plasma discharge device according to embodiments may include an insulating body; a discharge electrode formed in one or a first surface of the insulating body to generate plasma discharge; and a ground electrode formed in the other or a second surface of the insulating body to generate plasma discharge by reacting with the discharge electrode. The insulating body may be formed of or include a flexible material to be curved at a prescribed or predetermined curvature.

In order to allow plasma discharge to be generated with a relatively low voltage, the insulating body may have a thickness of dozens of micrometers. In order to ensure high-density radicals and a large discharge area, branches of the discharge electrode may be formed to have a width of dozens of micrometers. Further, in order to ensure plasma discharge stability, the plurality of branches forming a pattern of the discharge electrode may be arranged at uniform intervals, Non-patterned portions existing between the branches may be formed to have a prescribed or predetermined width.

Any reference in this specification to "one embodiment," "an embodiment," "example embodiment," etc., means that a particular feature, structure, or characteristic described in connection with the embodiment is included in at least one embodiment. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An air conditioner comprising:
    a main body having an air inlet through which air is suctioned into the main body and an air outlet through which air suctioned in through the air inlet is discharged from the main body after being conditioned;
    a fan provided in the main body to cause air to flow;
    a discharge vane configured to guide air discharged from the air outlet and formed such that an inner surface facing an inside of the main body is curved; and
    a plasma electrode device provided in a path of air flow generated by the fan to generate a large amount of ions, wherein the plasma electrode device includes:
    an insulating body;
    a discharge electrode formed in a first surface of the insulating body to generate plasma discharge; and
    a ground electrode formed in a second surface of the insulating body to generate plasma discharge by reacting with the discharge electrode, wherein the discharge electrode includes a prescribed pattern having a plurality of branches, and wherein the insulating body includes a flexible material configured to be curved at a predetermined curvature, wherein the plasma electrode device is mounted on the inner surface of the discharge vane and is curved corresponding to a shape of the inner surface of the discharge vane.

2. The air conditioner of claim 1, wherein the insulating body has a thickness of dozens of micrometers.

3. The air conditioner of claim 1, wherein the insulating body includes polyimide resin.

4. The air conditioner of claim 1, wherein the plurality of branches of the discharge electrode has a width of dozens of micrometers.

5. The air conditioner of claim 1, wherein the discharge electrode and the ground electrode are formed by depositing a metal plate on the insulating body and performing etching such that the discharge electrode has the prescribed pattern.

6. The air conditioner of claim 1, wherein the prescribed pattern of the discharge electrode has a non-patterned portion in which no electrode is formed.

7. The air conditioner of claim 6, wherein the non-patterned portion has a prescribed width between the plurality of branches such that the plurality of branches is arranged at uniform interval.

* * * * *